(12) United States Patent
Morris et al.

(10) Patent No.: US 6,180,762 B1
(45) Date of Patent: Jan. 30, 2001

(54) GLYCYRRHETINIC-ACID-LIKE FACTOR

(76) Inventors: David J. Morris, Washington St., Barrington, RI (US) 02806; Syed Abdul Latif, 58 Roberta Ave., Pawtucket, RI (US) 02860

(*) Notice: Under 35 U.S.C. 154(b), the term of this patent shall be extended for 0 days.

(21) Appl. No.: 09/476,851

(22) Filed: Jan. 3, 2000

Related U.S. Application Data

(63) Continuation of application No. 08/729,311, filed on Oct. 15, 1996, now Pat. No. 6,010,721, which is a continuation of application No. 08/395,163, filed on Feb. 27, 1995, now abandoned, which is a continuation of application No. 08/104,799, filed on Aug. 11, 1993, now abandoned, which is a continuation-in-part of application No. 07/764,819, filed on Sep. 24, 1991, now abandoned.

(51) Int. Cl.$^7$ .................................................. C07K 16/18
(52) U.S. Cl. ..................... 530/389.1; 530/388.1; 530/388.2; 530/388.24; 530/388.9; 530/389.2; 530/389.8
(58) Field of Search ............................. 530/389.1, 389.2, 530/389.8, 388.1, 388.2, 388.24, 388.9

(56) References Cited

U.S. PATENT DOCUMENTS 3,070,623 * 12/1962 Gottfried et al. .................... 502/403

OTHER PUBLICATIONS

E. Sevier et al. Clin. Chem., vol. 27, No. 11, 1797–1806 (1981).*

Kanaoka et al., Chem. Pharm. Bull., 29(6), 1533–1538 (1981).*

M. Kanaoka et al., Chem. Pharm. Bull 36(9), 3264–3270 (1988).*

Davis and Morris, "Medicinal uses of licorice through the millennia:the good plenty of it", *Molecular and Cellular Endocrinology* 78 pp. 1–6 (1991).

Morris et al., "Detection of Glycyrrhetinic Acid–Like Factors (GALFs) in Huma Urine", *Hypertension* 20(3) pp. 1–5 (1992).

Harlow and Lane, "Monoclonal Antibodies", *Antibodies A Laboratory Manual*, Chapter 6 p. 141 (Cold Spring Harbor Laboratory, New York) (1988).

* cited by examiner

*Primary Examiner*—Mary E. Ceperley
(74) *Attorney, Agent, or Firm*—Lahive & Cockfield, LLP

(57) ABSTRACT

A human glycyrrhetinic-acid-like factor which inhibits certain enzymes in pathways of steroid hormone degradation is disclosed.

1 Claim, 6 Drawing Sheets

# GLYCYRRHETINIC-ACID-LIKE FACTOR

RELATED APPLICATIONS

This application is a continuation application of Ser. No. 08/729,311 filed on Oct. 15, 1996, U.S. Pat. No. 6,010,721 which in turn is continuation of Ser. No. 08/395,163 filed Feb. 27, 1995 abandoned, which is in turn a FWC of serial no. 08/104,799 filed Aug. 11, 1993, abandoned which in turn is a continuation in part of Ser. No. 07/764,819 filed Sep. 24, 1991, abandoned. The contents of all of the aforementioned application(s) are hereby incorporated by reference.

GOVERNMENT SUPPORT

The work leading to this invention was supported, in part, by research grants from the U.S. government.

BACKGROUND

Glycyrrhetinic Acid (GA), the active principal in liquorice root, has been shown to markedly inhibit 11β-hydroxysteroid dehydrogenase (11β-OHSD) and steroid 5β-reductase when incubated with these enzymes (Stewart, P. M. et al. (1987) *Lancet* 2:821–823; Monder, C. et al. (1989) *Endocrinology* 125:1046–1053; Latif, S. A. et al. (1990) *Steroids* 55:52–58). The importance of both these enzymes has become apparent following the experiments of Ulick, New, Monder and co-workers (Ulick, S. et al. (1979) *J. Clin. Endocrin. Metab.* 49:747–764; New, M. I. et al. (1982) *Endocrinology of Hypertension, Serono Symposium*, vol. 50, pp 85–101; Monder, C. et al. (1986) *J. Clin. Endocrin. Metab.* 63:550–557) who demonstrated that hypertensive children with the syndrome of apparent mineralocorti-coid excess (AME) lack both 11β-OHSD and 5β-reductase activity. Alteration in these enzymatic pathways of steroid inactivation was shown to result in changes in the peripheral metabolism of cortisol. It has been postulated that higher peripheral and intrarenal concentrations of cortisol may then interact with mineralocorticoid receptors and promote sodium reabsorption (Edwards, C. R. W. et al. (1988) *Lancet* 2:986–989; Funder, J. W. et al. (1988) *Science* 242:583–585).

AME patients exhibit sodium retention, potassium wasting, and increased blood pressure without measurably increased circulating aldosterone. A pharmacological equivalent of this congenital condition results from the ingestion of liquorice which contains glycoside derivatives of GA (Stewart, P. M. et al. (1987) *Lancet* 2:821–823; Edwards, C. R. W. et al. (1988) *Lancet* 2:986–989). Because of the importance of these enzymes, it is possible that other categories of hypertension may also result from less extreme alterations of their activities.

SUMMARY OF THE INVENTION

This invention pertains to an endogenous human glycyrrhetinic-acid-like factor(s) or GALF(s) which inhibits hepatic and renal 11β-hydroxysteroid dehydrogenase (11β-OHSD) and hepatic 5β-steroid reductase (5β-SR). The factor(s) is isolatable from urine, is water soluble, is not extractable from aqueous solution into ethyl acetate and is resistant to heat and to trypsin treatment. Measurement of this factor will be useful for identification of individuals, particularly those with hypertension, who have altered enzymatic pathways for the inactivation of steroid hormones, such as cortisol and aldosterone, and may have a steroid component to, and which may be responsible for, their hypertension.

DETAILED DESCRIPTION OF THE INVENTION

Figure 1A:
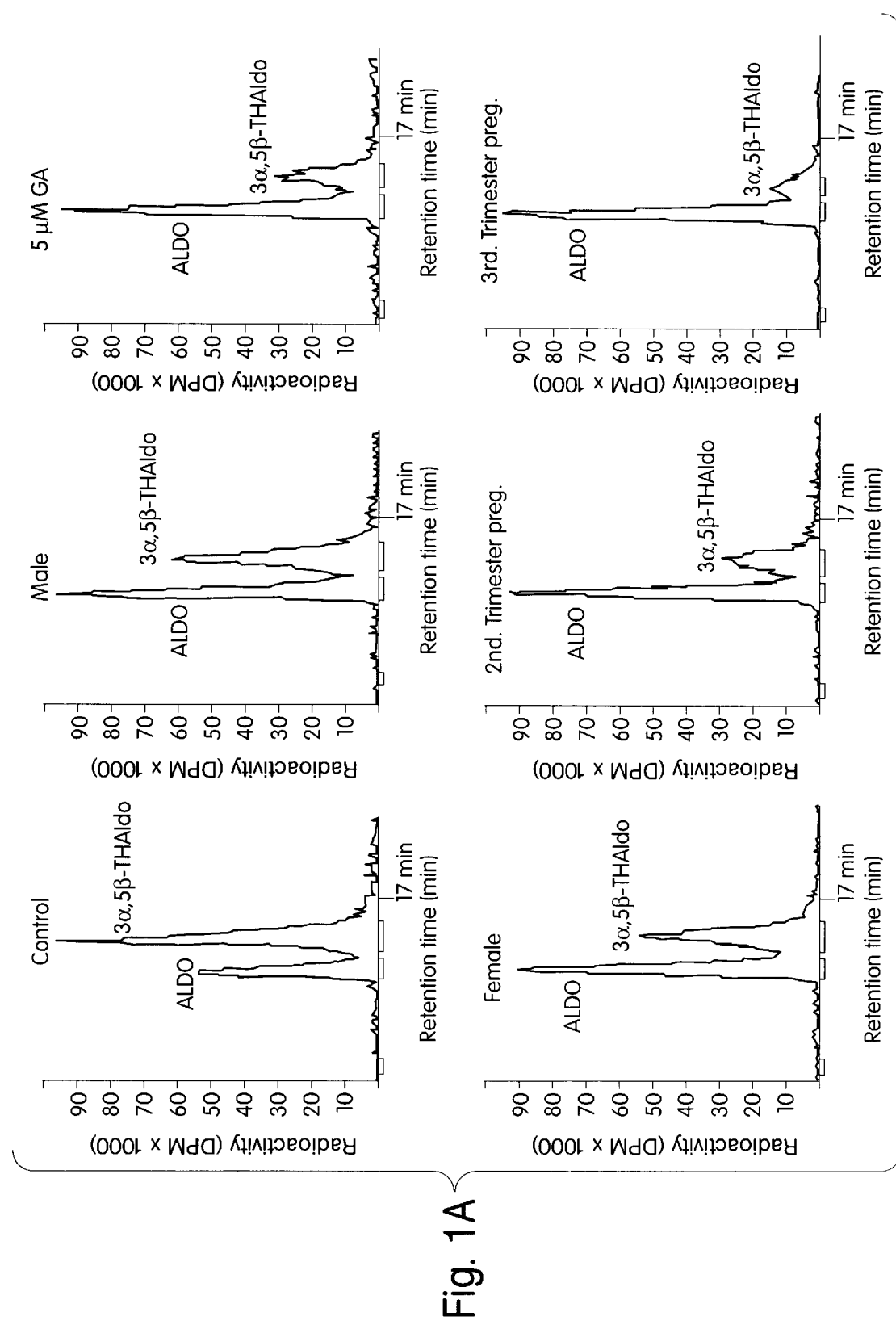
FIG. 1 shows the inhibition of hepatic, cytosolic 5β-reductase and microsomal 11β-OHSD by the glycyrrhetinic-acid-like factor(s) (GALF).

Urine from normotensive individuals contains at least two substances, or groups of substances, designated glycyrrhetinic-acid-like factor(s) or GALF(s), which markedly inhibit cytosolic 5β-SR and microsomal 11β-OHSD. These substances are referred to herein as 11β-GALF for substance(s) active against 11β-OHSD and 5β-GALF for substance(s) active against 5β-SR. The presence of GALF factors was found in urines collected from individuals with congestive heart failure (CHF) and mild essential hypertension. In these individuals, there are increased amounts of both 11β- and 5β-GALF(s) compared to normotensive individuals. The majority of the GALF factor(s) is water soluble and is not extractable from aqueous solution into ethyl acetate, indicating that it does not consist of "free" urinary steroids such as cortisol, which would compete as a substrate in both enzyme reactions. In addition, the GALF factor(s) is heat stable, is resistant to trypsin digestion and does not react with ninhydrin. The factor(s) can be reproducibly resolved by gradient high performance liquid chromatography (HPLC) into at least two peaks which possess inhibitory activity. The characteristics of this material are described in detail in the exemplification below. The chemical structure of the isolated factor(s) can be ascertained by standard techniques such as gas chromatography-mass spectrometry.

Similar levels of the glycyrrhetinic-acid-like factor are present in urine from normotensive males and non-pregnant females but significantly higher quantities were present in urine of females in the second and third trimester of pregnancy. Despite differences in levels, the chromatographic profiles and other chemical properties were similar in all three groups.

The factor(s) of this invention are non-glycyrrhetinic-acid substances which inhibit enzymes involved in steroid degradation. Determining levels of the factor(s) may be useful for identification of individuals who have altered enzymatic pathways for the inactivation of steroid hormones such as mineral-ocorticoids (e.g., aldosterone) and glucocorticoids (e.g., cortisol). The levels of this factor(s) may be particularly important in hypertensives where altered levels of steroid degradation may be linked to hypertension.

The factor(s) can be assayed in biological fluids by immunochemical means using antibodies against the factor(s). Antibody against the factor(s) can be made by standard procedures. In general, the factor(s) is administered as an immunogen to an animal to generate an antibody response. If haptenic, it can be coupled to an appropriate carrier. Antibody can be harvested from the immunized animal as antiserum. Alternatively, monoclonal antibodies can be prepared by obtaining antibody producing cells (e.g., B-lymphocytes) from the immunized animal, fusing the antibody cells with immortalizing cells (e.g., myeloma cells) to produce hybridomas and screening the hybridomas for those that produce antibody against the factor(s).

The immunochemical assays can be competitive or immunometric (e.g., radiometric or enzymetric). In a competitive assay, for example, an antibody is reacted with a constant amount of labeled antigen and varying amounts of unlabeled antigen to produce a standard antibody-antigen binding curve. The sample is incubated with the antibody in the presence of the labeled antigen. Antibody bound antigen is separated from unbound antigen. The amount of labeled antigen bound by antibody is indicative of the amount of antigen (GALF) in the sample.

In a sandwich immunoactive assay, an antibody (in excess) is contacted with sample to capture antigen. Bound and unbound antigen are separated. Bound antigen is then determined by reacting a second antibody (which is either labeled or capable of being labeled). Bound antigen is directly proportional to the amount of antigen in the sample.

Solid phase formats of the immunochemical assays are preferred. Reagents for performance of the assays can be provided in the form of kits.

The invention is illustrated further by the following exemplification.

EXAMPLE I

Materials and Methods
Urine Samples

Random urine samples were donated by non-hypertensive male and female members of the laboratory and samples from healthy pregnant women on routine visits to their obstetrician. Urine samples were frozen until used. After thawing aliquots were centrifuged to remove any debris or precipitate and samples were assayed for their creatinine contents using a Beckman CX3 Analyser.

10 ml samples of the centrifuged urine were then passed onto previously activated Waters $C_{18}$ SepPaks (Waters Chromatography Division, Millipore Corp., Milford, Mass.) and were eluted first with 5 mls of water, which removed salts, proteins, and other strongly polar components, followed by 5 mls of 100% HPLC grade methanol. Preliminary experiments had shown that no "inhibitory" activity was lost in the initial water eluate. The methanol eluates were evaporated to dryness under nitrogen and then redissolved in 2 mls of distilled water to give a five-fold concentration of the original sample. Samples processed in this manner are referred to as 'Urine Samples' in the rest of this exemplification.

HPLC Gradient Separation of Components of Urine Samples 2 ml urine samples with a 30% methanol content were chromatographed on a 25×0.5 cm C18 5 mm reverse phase column (Isco Corp. Omaha, Nebr.). Components were eluted with a non-linear methanol/water gradient commencing with 30% methanol which increased linearly to 40% methanol at 400 secs.; 60% methanol at 1900 secs.; and 100% methanol at 2000 secs. 1 ml fractions were collected at a flow rate of 1 ml/min. The absorbance at 240 nm was monitored as a guide to the number of components present. Following separation, the 1 ml fractions were assayed for their "inhibitory" activity using the radio-enzymatic assay methods described below. Samples with marked "inhibitory" effect were also spotted onto Whatman filter paper, dried and sprayed with ninhydrin to detect the presence of peptides or other amines or sugar amines.

Modification of Urine Samples
Heat

Urine samples (pH 7.4) were heated at 100° C. for 10 mins. Both heated and unheated samples were then assayed for inhibitory activity.

Assay of "Inhibitory" Activity

Details of methods for the radioenzymatic assay of 5β-steroid reductase and 11β-OHSD, by measuring the conversion of $[1,2-^3H]$ aldosterone to 3a,5β-tetrahydroaldosterone for the first of these and the conversion of $[1,2-^3H]$ corticosterone to 11-dehydrocorticosterone for the latter have been previously described (Monder, C. et al. (1989) *Endocrinology* 125:1046–1053; Latif, S. A. et al (1990) *Steroids* 55:52–58). $[1,2-^3H]$-aldosterone and $[1,2-^3H]$-corticosterone with specific activities of 53.9 Ci/mmol and 56.4 Ci/mmol, respectively, were obtained from Dupont New England Nuclear (Boston, Mass.). Their purity was checked by HPLC before use. Methanol (HPLC-grade) was obtained from Fisher Scientific (Medford, Mass.). Dihydronicotinamide-adenine dinucleotide phosphate (NADPH), Trizma base (tris-hydroxymethyl-amminomethane), $NADP^+$, glycyrrhetinic acid (GA), corticosterone (Compound B) and 11β dehydrocorticosterone (Compound A) were obtained from Sigma Chemical Co. (St. Louis, Mo.) and aldosterone was obtained from Andard Mount (London, UK).

Both enzymes were prepared in crude form from the livers of normal adult male Sprague-Dawley rats (Charles River Breeding Laboratories, Wilmington, Mass.). Following sacrifice, the livers were rapidly removed, washed carefully with ice cold 0.25 M sucrose and microsomal and cytosolic fractions were prepared for measurements of 11β-OHSD and 5β-reductase enzymatic activities respectively as described below.

Livers were homogenized in 0.25 M sucrose (1:4 wt/vol) using a Teflon homogenizer and subcellular fractions were obtained by differential centrifugation at 4 C. using a Sorvall RC-2 preparative and Beckman L8-80 ultracentrifuge. The homogenate was centrifuged at 1,000×g for 10 mins. and the resultant supernatant from this and subsequent spins were recentrifuged first for 10 mins. at 10,000×g and then at 17,000×g, respectively. The 17,000×g supernatant was centrifuged at 105,000×g for 70 mins. and the microsomal pellet was rinsed with cold homogenization medium and resuspended in cold 0.25 M sucrose at a concentration of 30 mg protein/ml. The final supernatant is the liver cytosol preparation containing 5β-reductase (Latif, S. A. et at. (1990) *Steroids* 55:52–58) and the microsomal pellet is the source of 11β-OHSD activity (Monder, C. et al. (1989) *Endocrinology* 125:1046–1053).

Enzyme Assays
11β-OHSD Assay 0.14 mg of liver microsomal fraction was incubated at 37° C. for 10 mins. with 2 mM non-radioactive corticosterone and $^3H$-corticosterone (1 mC) as tracer in Tris-HCl buffer, pH 8.5, containing 3.4 mM $NADP^+$ in a total volume of 0.5 ml. Included in this volume is an aliquot either of water, in the case of controls, or of the aqueous extract from SepPak treated urine whose inhibitory activity is being measured. The enzymatic reaction was terminated by addition of 2 ml methanol. Synthesis of 11-dehydro-corticosterone was quantitated by HPLC as described below.

5β-Reductase Assay

Aliquots of cytosol were incubated with 5 mM aldosterone and 1 mCi of [$^3$H]-aldosterone in 50 mM Tris-HCl buffer (pH 7.4), 5 mM $MgCl_2$, 2.76 mM NADPH and 2% ethanol in a final volume of 0.5 ml. Again, appropriate aliquots of water and urine samples were added. The reaction mixtures were incubated at 37° C. for 10 mins. and again terminated by the addition of 2 ml methanol. Synthesis of 3a,5β-tetrahydroaldosterone was quantitated by HPLC as described below.

Estimation of Enzyme Activity

The methanol extracts of the incubation media were centrifuged at 1000×g for 10 mins. 0.5 ml aliquots of supernatant were evaporated to dryness under $N_2$, dissolved in 20% MeOH and chromatographed on a Dupont Zorbax C8 reversed-phase column, at 44° C. with 45 % aqueous-methanol (isocratic) at a constant flow rate of 1 ml/min. This system separated both Compound B from Compound A and also aldosterone from 3a,5β-tetrahydroaldosterone. The radioactive metabolite peaks were detected by an on-line β-detection system (model LB-504, Berthold Instrument, Nashua, N.H.) after mixing of the HPLC column eluate with scintillation fluid (Ultima-Gold, Packard Instruments, Downers Grove, Ill.) with a 10% counting efficiency under conditions of flow. Following substraction of background radioactivity, the percentage distribution of radioactivity among all HPLC peaks in each chromatogram was determined. The enzyme activity was then calculated and expressed either as nmol or ng of product made/10 mins.

Calculation of Inhibition

Inhibition was calculated in two ways. In the case of aliquots from the HPLC gradient separations inhibition was calculated as the percentage reduction in apparent enzyme activity in the test sample as compared with the control. Samples of whole urine yielded similar data but the results were also expressed as 'GA equivalent' units. For this purpose aliquots of GA were added to the incubation mixtures at varying concentrations up to 10 mM and the degree of inhibition calculated. From this data a GA inhibitory standard curve could be plotted and the 'GA equivalent' units contained in the test sample of urine calculated.

Results

Measurement of Total Urinary "Inhibitory" Activity

The aim of these experiments was to investigate whether GALF factor(s) can be detected and measured in human urine. Random urines were obtained from 5 males, 7 from non-pregnant females and 9 from females in the second and third trimesters of pregnancy. Aliquots of urine from these subjects were measured for their abilities to inhibit the two enzymes, 5β-reductase and 11β-OHSD. Known amounts of GA (0.1–10 mM) standards were also added to control incubation mixtures to define two standard "inhibition" curves related to the % inhibition of each of the enzymes. From these results, and the initial urinary creatinine measurements, we have expressed the "inhibitory" activity as mg equivalents of GA per mg of creatinine, (5β-GA-Units and 11β-GA-Units, respectively) in each urine sample.

The "inhibitory" material(s) in each urine sample were extracted using SepPak $C_{18}$ Bondapak, following desalting with $H_2O$. Using the hepatic cytosolic 5β-reductase radioenzymatic assay which measures the fraction of [$^3$H]-aldosterone converted to [$^3$H]-3a,5β tetrahydroaldosterone, the "inhibitory" activity ranged from 1.0 to 2.1 5β-GA-Units (mean=1.48) for males; from 1.4 to 2.1 5β-GA-Units for non-pregnant females; from 3.7 to 10.9 5β-GA-Units for second trimester pregnant females; and from 10.3 to 31.0 5β-GA-Units for third trimester pregnant females (Table 1).

Using the hepatic microsomal 11β-OHSD radioenzymatic assay which measures the proportion of [$^3$H]-Compound B converted to [$^3$H]-Compound A the "inhibitory" activity was from 0.07 to 0.22 (mean=0.15) 11β-GA-Units for males; from 0.11 to 0.36 (mean=0.23) 11β-GA-Units for non-pregnant females; and from 0.39 to 0.55 (mean=0.43) 11β-GA-Units in the second trimester and from 0.44 to 1.09 (mean=0.72) 11β-GA-Units in the third trimester (Table 1).

There is no statistically significant difference between males and non-pregnant females or either enzyme, and both groups have significantly less "inhibitory" activity than any of the pregnant females.

TABLE 1

"Inhibitory" Activity of Urine Extracts

| Urine source | Inhibition of 5β-reductase (5β-GA-Units) | Inhibition of 11β-OHSD (11β-GA-Units) |
| --- | --- | --- |
| Females | | |
| Non-pregnant | 1.80 ± 0.36 | 0.25 ± 0.08 |
| Second trimester | 6.65 (3.7–10.9)* | 0.43 (0.39–0.55) |
| Third trimester | 16.6 (10.8–31) | 0.72 (0.44–1.09) |
| Males | 1.48 + 0.42 | 0.15 + 0.05 |

Urines were extracted by $C_{18}$ SepPak cartridges and assayed for "inhibitory" activity against 5β-reductase and 11β-OHSD. Glycyrrhetinic acid equivalent units were expressed as mg GA/mg creatinine. A dose-response curve for the "inhibitory" activity of GA (0–10 mM) was constructed. (1 GA Equivalent Unit=the amount of inhibitor present in urine extract which inhibits enzyme activity equal to that of 1 mg GA). Values are mean ±SD. *Values in parenthesis represent range. (n=4–7).

Figure 1B:
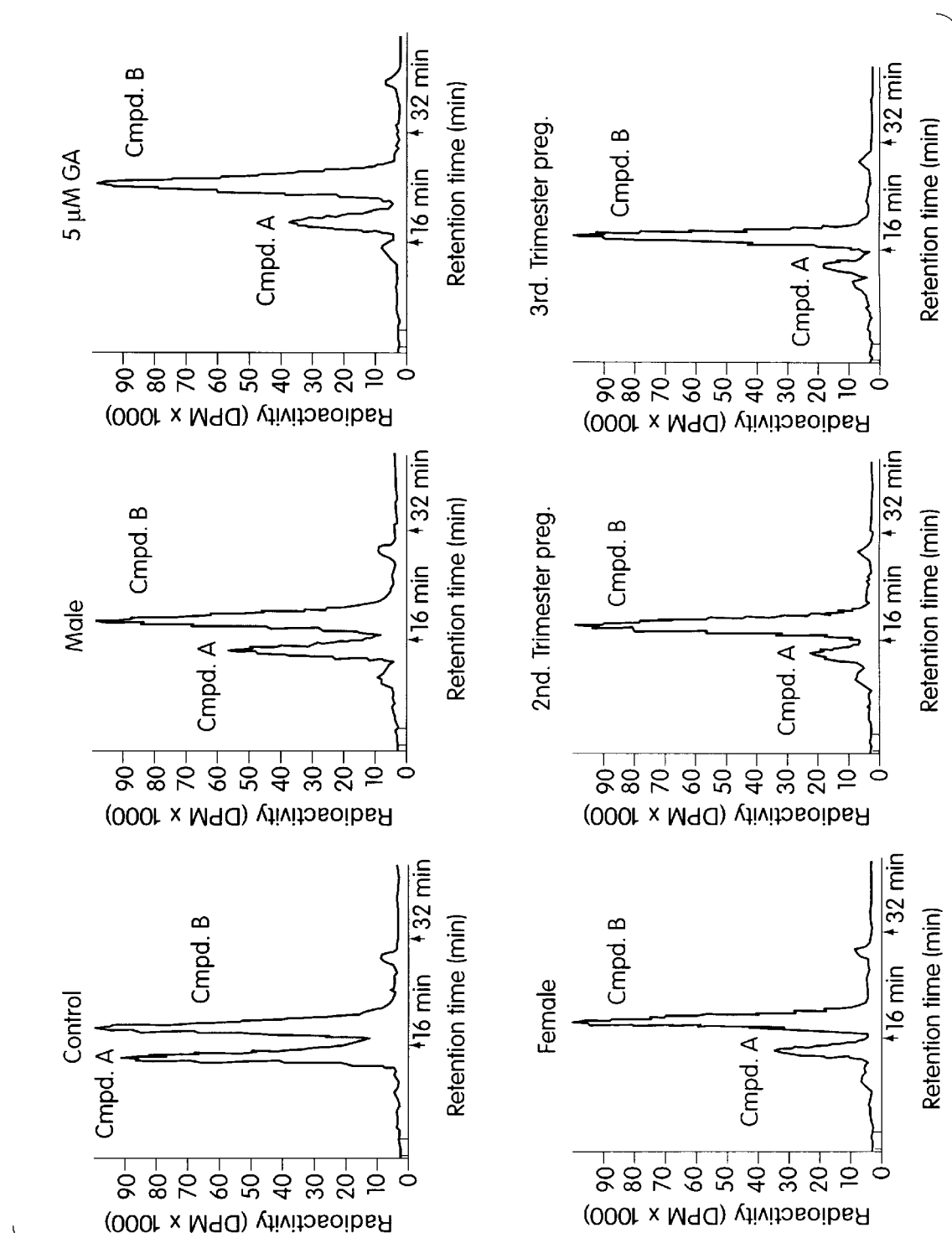

FIG. 1 shows representative chromatograms depicting the extent of enzymatic conversion of "PANEL A" aldosterone to 3a,5β-tetrahydroaldosterone, "PANEL B " corticosterone (Compound B) to 11-dehydrocortico-sterone (Compound A), when assayed together with "inhibitors" extracted from human urine: (a) control, no extract; (b) male; (c) glycyrrhetinic acid; (d) female; and (e & f) pregnant female.

Chromatographic Separation of Urinary "Inhibitory" Activity

The SepPak extracted "inhibitory" material from each group of urines was then chromatographed by reverse phase HPLC using a programmed gradient of aqueous methanol (FIG. 2) resulting in 33×1 min. fractions. Each 1 ml fraction was assayed for "inhibitory" activity against both 5β-reductase and 11β-OHSD radioenzymatic assays. Results were expressed as relative % inhibition, rather than as GA-Units. Two major regions of "inhibitory" activity were resolved from the original urine extracts using these elution gradients. The first major peak of activity was found in the fractions eluting between 6 and 9 mins. (34–38% methanol). A second, much sharper peak, eluted at 17–18 mins. (46–47% methanol).

Similar elution patterns of "inhibitory" activity were observed for male, female and pregnant urines using this HPLC gradient. These initial results do not as yet permit us to generalize on the relationships between the inhibitory components in urines from different sources.

Chemical Classification of "Inhibitory" Activity

Sensitivity to Heat

No reduction in "inhibitory" activity of any of the samples occurred when urine samples, buffered to pH 7.4 with Tris-HCl, were heated for 10 mins. in boiling water. Overnight incubation of samples at 37° C. in pH 5.2 acetate buffer was also without effect.

Reactions with Ninhydrin

Unfractionated urine samples showed slight ninhydrin positivity, but fractions containing "inhibitory" activity eluted from the HPLC gradient were unreactive.

Extractability

Attempts to extract the "inhibitory" activity from the urine samples directly into ethyl acetate were not successful with the majority of the activity remaining in the aqueous phase.

EXAMPLE II

Glycyrrhetinic-Like Factors in the Urine of Patients with Congestive Heart Failure Materials and Methods Collection of Urine Samples Twenty-four hour samples of known volume and creatinine content were collected from the Memorial Hospital, Pawtucket, R.I. (mild essential hypertension) and the Miriam Hospital, Providence, R.I. (congestive heart failure; CHF). All samples were kept frozen in the laboratory prior to processing and analysis. Samples were collected on a voluntary basis using the system of informed consent appropriate to each location. Both sites excluded individuals with physical or laboratory findings suggestive of secondary hypertension, liver or renal diseases, diabetes mellitus, obesity, or abuse of alcohol or drugs. All medication was withheld from all hypertensive patients from Pawtucket for four weeks prior to the collection of their urines.

Selection of Subjects

A. The Memorial Hospital

Fourteen patients (12 men and 2 women), 18 to 75 years old, were recruited for a clinical research trial on the treatment of mild hypertension. Subjects conformed to the selection criteria given above and in addition all subjects with diastolic pressures >105 mm Hg. were excluded from the study. Nine healthy adults, aged 22 to 53, without known hypertension were selected as controls.

B. The Miriam Hospital

Fourteen patients with CHF, characterized by pulmonary edema and hypoxia (9 men and 5 women), 53 to 86 years old were recruited by a staff cardiologist. Seven healthy adults, aged 34 to 53, were used as controls in this study.

Analysis of Urine Samples

Urine creatinine concentrations were assayed using a Beckman CX3 Analyzer. Ten ml. urine samples were desalted and partially purified by extraction onto $C_{18}$ Sep-Pak cartridges (Waters Chromatography Division of Millipore Corp., Milford, Mass.), and urine extracts prepared (FIGS. 2 to 5) as previously described above (see also, Morris, D. J. et al (1992) *Hypertension* 20:356–360).

Assay of "Inhibitory" Activity

Radioenzymatic assay of 5β-steroid reductase was performed by measuring the conversion of [$^3$H]-aldosterone to its 3α, 5β-tetrahydro derivative and 11β-OHSD by measuring the conversion of [$^3$H]-corticosterone to [$^3$H]-11-dehydrocorticosterone as previously described (Monder, C. et al. (1989) *Endocrinology* 125:1046–1053; Latif, S. A. et al. (1990) *Steroids* 55:52–58). [1,2-$^3$H]-Aldosterone (Aldo) and [1,2-$^3$H]-Corticosterone with specific activities of 53.9 Ci/mmol and 56.4 Ci/mmol, respectively were obtained from Dupont New England Nuclear (Boston, Mass.). Their purity was checked by HPLC before use. Methanol (HPLC grade) was obtained from Fisher Scientific (Medford, Mass.). Nicotinamide-adenine dinucleotide phosphate, reduced form (NADPH), Trizma base (tris-hydroxymethyl-aminomethane), NADP$^+$, glycyrrhetinic acid (GA), corticosterone (Compound B), and 11-dehydrocorticosterone (Compound A) were obtained from Sigma Chemical Co. (St. Louis, Mo.) and Aldo was obtained from Andard Mount (London, UK).

Both enzymes were prepared in crude form from the livers of the adult male Sprague-Dawley rats (Charles Rivers Breeding Laboratories, Wilmington, Mass.). Livers were rapidly removed, washed with ice cold 0.25 M sucrose, and microsomal and cytosolic fractions were prepared for measurements of 11β-OHSD and 5β-reductase enzymatic activities respectively using a modification of the previously described methods (Morris, D. J. et al. (1992) *Hypertension* 20:356–360).

11β-OHSD Assay

Liver microsomes (0.07 mg protein) were incubated at 37° C. for 10 min. with 5 μM corticosterone and $^3$H-corticosterone (1 μCi) as tracer in 50 mM Tris-HCl buffer (pH 8.5), containing 3.4 mM NADP$^+$ in a total volume of 0.25 ml. Included in this volume is an aliquot of either water (controls), urine extracts, or GA. The reaction was terminated by addition of 1 ml methanol. Synthesis of 11-dehydrocorticosterone was quantitated by HPLC (Morris, D. J. et al. (1992) *Hypertension* 20:356–360).

5β-reductase Assay

Aliquots of cytosol (approximately 2 mg protein) were incubated with 45 μM Aldo and [$^3$H]-Aldo (1 μCi) in 50 mM Tris-HCl buffer (pH 7.4), 5 mM $MgCl_2$, 2.76 mM NADPH, and 2% ethanol in a final volume of 0.25 ml. Appropriate aliquots of water (controls) or urine extracts or GA were added. The reaction mixtures were incubated at 37° C. for 10 min. and terminated with 1 ml methanol. Synthesis of 3α, 5β-tetrahydro-Aldo was quantitated by HPLC (Morris, D. J. et al (1992) *Hypertension* 20:356–360).

Calculation of Inhibition

To provide a basis for the quantitation of urine "inhibitory" activity, aliquots of GA were added to control incubation mixtures (volume 0.25 ml) in varying amounts (0–1.2 μg for 5β-reductase and 0–0.012 μg for 11β-OHSD) and percent inhibition was calculated relative to controls (without GA) as previously described. Briefly, percent inhibition due to urine extract was converted to μg GA (GA equivalent units) using the appropriate GA standard curve. These GA equivalent units were expressed as μg GA/mg creatinine to normalize them for dilute or concentrated urine. Note that because of the different values of $K_i$ for GA inhibition of 5β-reductase and 11β-OHSD, and because the two enzymes were measured in two different bioassay systems, the magnitude of the GALF units is different for the two enzymes. Therefore, we designate them as 5β-GALF Units and 11β-GALF Units.

Results

1. Congestive Heart Failure

Figure 2:
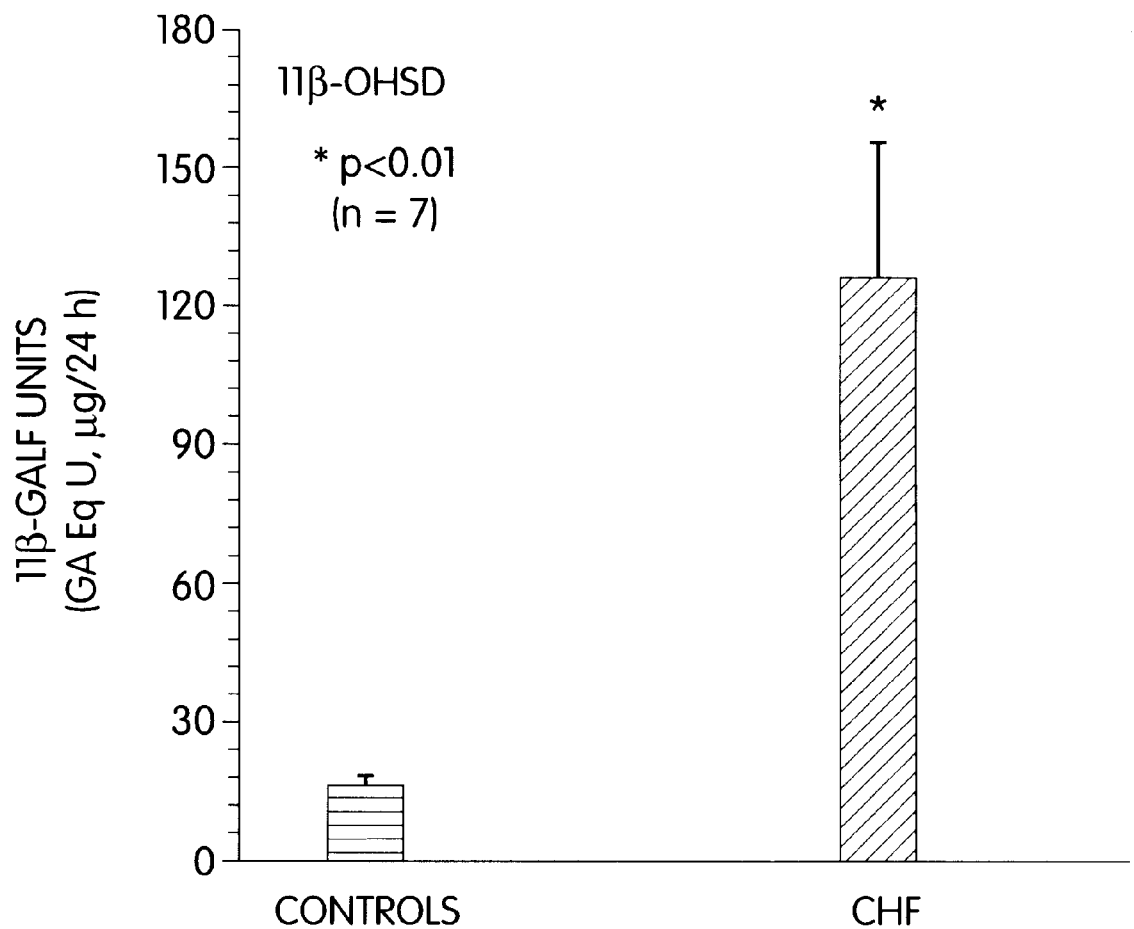
FIG. 2 is a bar graph showing levels of 11β-GALF units (GA-equivalent units, µg/24 hr) in urine from patient with congestive heart failure (CHF) and control subjects. Values represent means ±S.E.M.*$p<0.01$, n=7.
Figure 3:
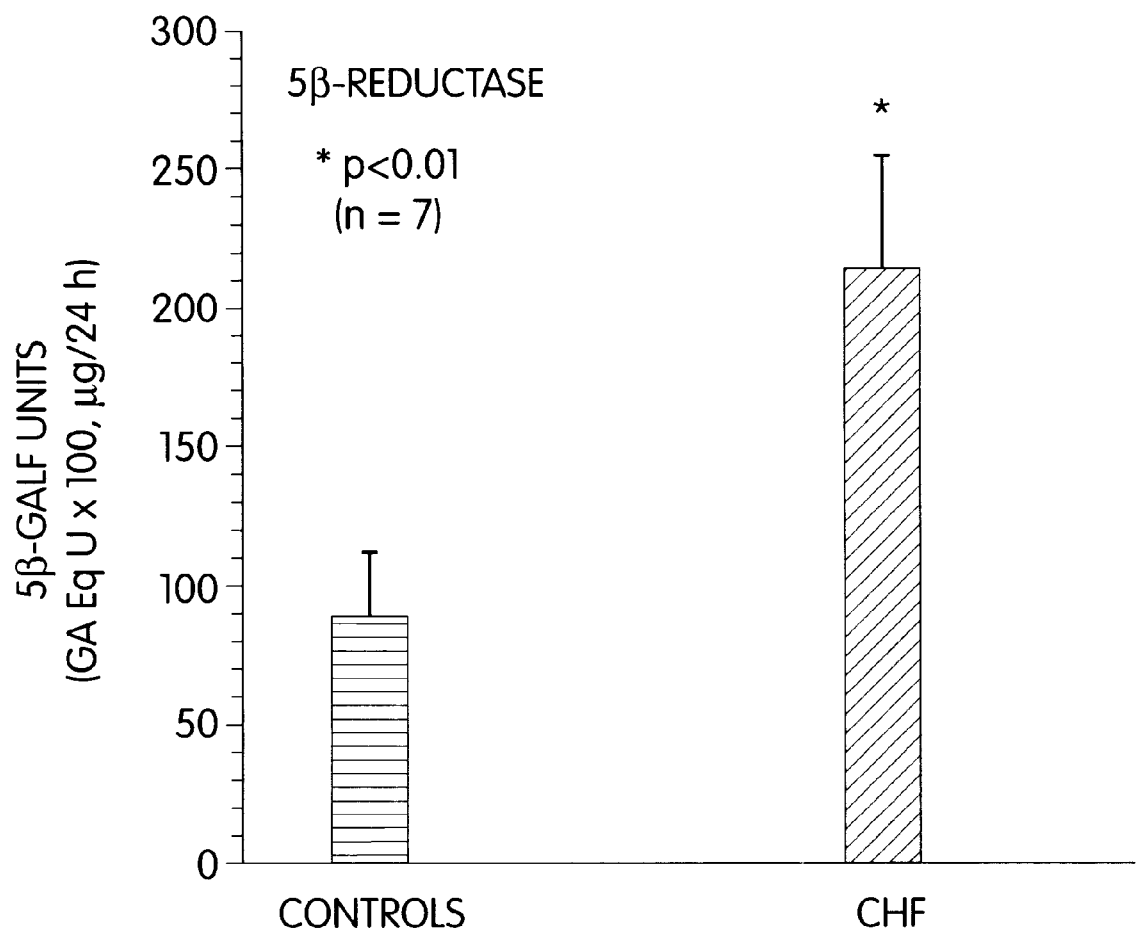
FIG. 3 is a bar graph showing levels of 5β-GALF units (GA-equivalent units, µg/24 hr) in urine from patient with congestive heart failure and control subjects. Values represent means ±S.E.M.*$p<0.01$, n=7).

FIGS. 2 and 3 show the number of units of 11β-GALF and 5β-GALF in urine from subjects with CHF as compared with controls. The mean increase for both enzymes is highly significant (p<0.01), with 11β-GALF rising approximately 600% and 5β-GALF increasing to 225%.

2. Essential Hypertension

Figure 4:
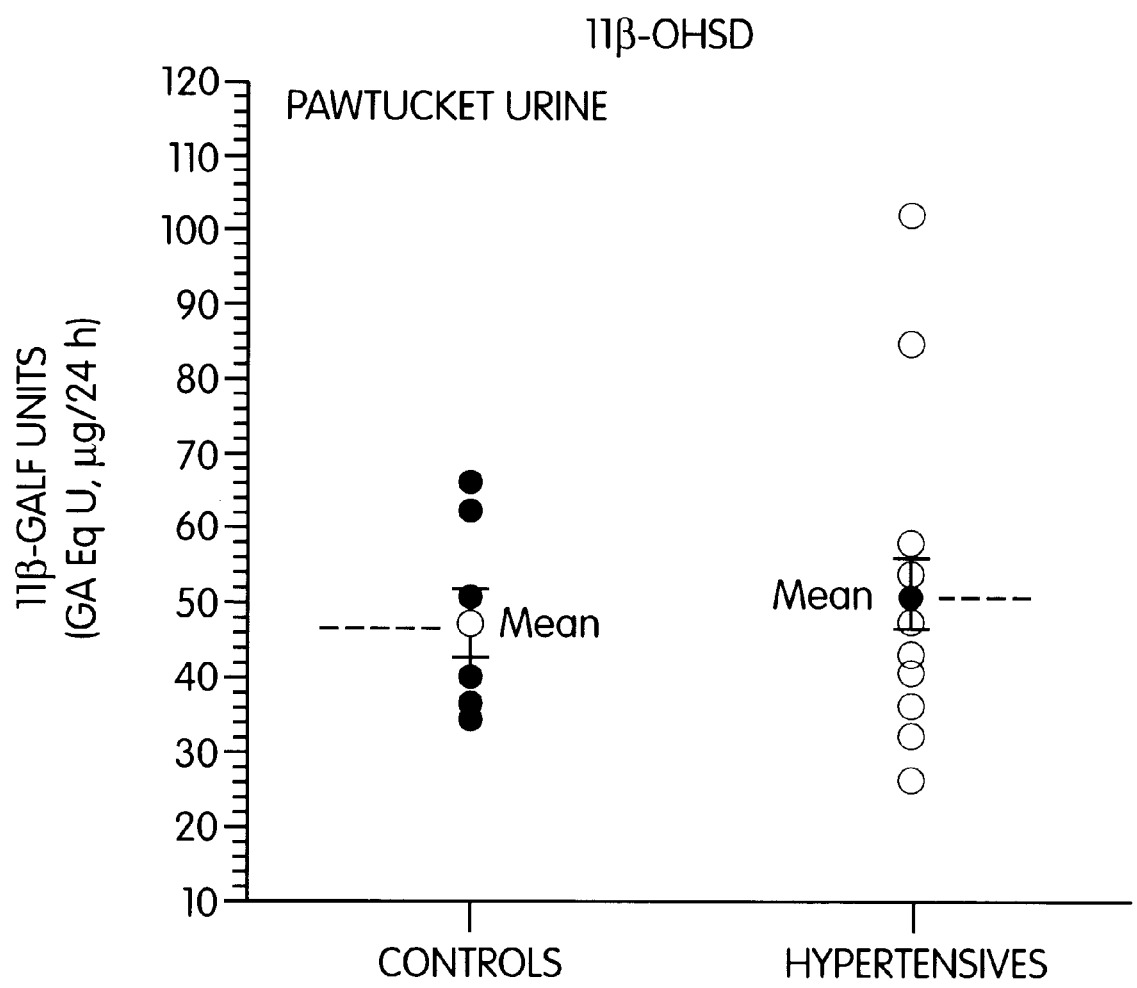
FIG. 4 is a bar graph showing levels of 11β-GALF units (GA-equivalent units, µg/24 hr) in urine from patient with mild essential hypertension and normotensive subjects. Values represent means ±S.E.M. (n=7–14).
Figure 5:
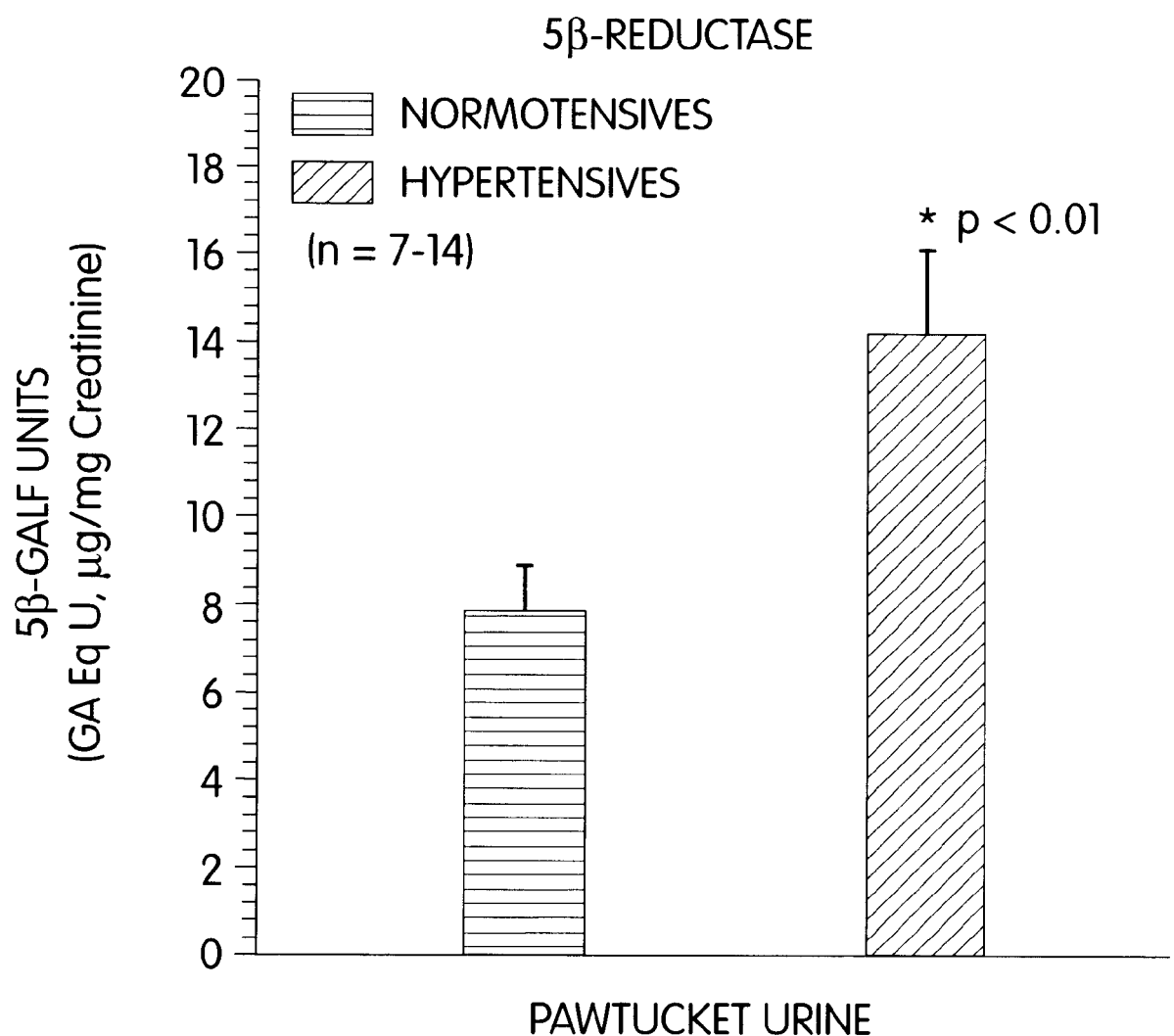
FIG. 5 is a bar graph showing levels of 5β-GALF units (GA-equivalent units, µg/mg creatinine) in urine from patients with mild essential hypertension and normotensive subjects. Values represent means ±S.E.M.*$p<0.01$, n=7–14.

FIGS. 4 and 5, showing urinary 11β-GALF and 5β-GALF activity in essential hypertension, present a different picture. There is signifcant increase (p<0.01) in urinary 5β-GALF in the hypertensive group as compared with the normotensive group (FIG. 4). By contrast, there is no statistically significant difference between the urinary 11β-GALF levels in essential hypertension as compared with the control group. However, the scatter of the results from hypertensive patients is much greater than the scatter for normotensive (FIG. 4). In particular, there are elevated outliers which suggest the possibility that there may be a specific subset of essential hypertensives who may indeed consistently excrete elevated levels of both 5β- and 11β-GALFs in their urine.

Discussion

Diminished activity of the enzyme 11β-OHSD leading to decreased rates of inactivation of cortisol to cortisone has been suggested to account for the increased $Na^+$ retention, hypokalemia and increased B.P. in patients with AME (Ulick, S. et al. (1979) *J. Clin. Endocrinol. Metab.* 49:747–764; New, M.I. (1982) In: Mantero, F., Biglieri C., Edwards, C. R. W. (eds): *Endocrinology of Hypertension.* Serono Symposium 50:85–101). These patients were also shown to have decreased 5β-SR activity (Monder, C. et al. (1986) *J. Clin. Endocrin. Metab.* 63:550–557). Ingestion of liquorice, which is also associated with similar clinical features, also leads to lower activities of both these enzymes (Stewart, P. M. et al. (1987) *Lancet* 2:821–823). Since in vitro, glucocorticoids have equal affinity for mineralocorticoid receptors as mineralocorticoids such as aldosterone but do not normally activate these receptors in vivo, 11β-OHSD-mediated inactivation of cortisol and corticosterone has been suggested to play a major role in protecting mineralocorticoid receptors from glucocorticoids and thereby regulating electrolyte balance and blood pressure (Edwards, C. R. W. et al. (1988) *Lancet* 2:986–989; Funder, J. W. et al (1988) *Science* 242:583–585). As described herein, urine from normotensive males and females contains measurable levels of 11β-GALF and 5β-GALF, and that both of these increase significantly throughout pregnancy with its marked changes in electrolyte and water homeostasis. The levels of 11β-GALF and 5β-GALF were determined in the urines of patients with CHF and essential hypertension. In these experiments, one patient with essential hypertension and another with CHEF were chosen. All patients with CHF showed consistent and marked increases in their urinary output of both 11β- and 5β-GALF output. The hypertensive group had had their medication withheld for 8 weeks. These patients all had increased levels of 5β-GALF activity both in terms of their concentration in the urine and also the total amount excreted in the 24 hr. urine samples. However, only a small number of these patients, possibly a physiological subset of this group also showed increases in the concentration and total amount of 11β-GALF excreted in their 24 hr. urine samples.

The present experiments indicate that two additional groups of patients in which increased mineralocorticoid activity might be necessary to maintain electrolyte and water balance. Increasing the half-lifes of both glucocorticoids and mineralocorticoids by inhibiting their catabolic enzymes might provide such increased mineralocorticoid activity.

The studies described herein demonstrate that GALF substance(s) can be reproducibly measured and which may represent undescribed endogenous factor(s) involved in the regulation of steroid metabolism. These factors may affect the extent of (a) 11β-hydroxy oxidation by 11β-OHSD and/or (b) Ring A-reduction by 5β-SR of cortisol and possibly other adrenal steroid hormones. The results described herein may provide an explanation for previously observed alterations in the urinary metabolite tetrahydrocortisol/tetrahydrocortisone ratios in essential hypertensives (Lewicka, S. et al. (1991) *N.Y. Acad. Sci.* 595:435–440; Walker, B. R. and Edwards, C. R. W. (1991) In: Edwards C. R. W. and Lincoln, D. W. (eds): *Recent Advances in Endocrinology and Metabolism* 4:21–32; Kornel, L. and Margolis, E. (1992) Abstract 04.31.023 IXth. International Congress of Endocrinology, Nice), and changes in the plasma half-life of $11\alpha$-$^3H$-cortisol in these patients (Walker, B. R. and Edwards, C. R. W. (1991) In: Edwards C. R. W. and Lincoln, D. W. (eds): *Recent Advances in Endocrinology and Metabolism* 4:21–32), suggestive of 11β-OHSD deficiency, in patients with essential hypertension. The presence of GALFs in these patient may be linked to changes in the handling of glucocorticoids and mineralocorticoids in many sites, including liver and kidney. Additional evidence for such a concept is provided by the demonstration that treatment of adrenalectomized male rats with carbenoxolone sodium, a succinate derivative of GA, caused the glucocorticoids of corticosterone and cortisol to display minearlocorticoid like activity (Souness, G. W. and Morris, D. J. (1989) *Endocrinology* 124:1588–1590) and also amplified the $Na^+$ retaining properties of the minearlocorticoids aldosterone and deoxycorticosterone (Morris, D. J. and Souness, G. W. (1990) *Am. J. Physiol.* (Renal Fluid Electrolyte Physiol.) 258:F756–F759).

In conclusion, the results described herein indicate that endogenous factors produced in excess by patients with essential hypertension may alter corticosteroid metabolism thus amplifying tissue sensitivity to cortisol and perhaps also to aldosterone and deoxycorticosterone and contributing to the elevation of blood pressure in these patients.

EXAMPLE III

Various endogenous substances which bear similar structural resemblances to glycyrrhetinic acid (GA) were screened for inhibitory activity against 11β-hydroxysteroid dehydrogenase (11β-OHSD) and 5β-reductase (5β-R). Among the compounds screened 3α,5β-tetrahydrodeoxycorticosterone (3α,5β-THDOC) was the most potent inhibitor of both 11β-OHSD and 5β-R. Of the bile acids tested, chenodeoxycholic acid (CDCA) was the most potent inhibitor of both 11β-OHSD and 5β-R. Although lithocholic acid (LCA) was a potent inhibitor and cholic acid (CA) a moderate inhibitor of 11β-OHSD, both bile acids were weak inhibitors of 5β-R, whereas deoxycholic acid (DCA) was a moderate inhibitor of 5β-R but a weak inhibitor of 11β-OHSD.

3α,5β-THDOC and bile acids were also treated to determine whether, like GA, they could confer mineralocorticoid (MC) actions upon corticosterone. In adrenalectomized rats pretreated with CDCA, corticosterone caused a significant antinatriuresis; this effect was blocked by the antimineralocorticoid, RU28318. Thus, there appears to be three structurally similar endogenous substances, 3α,5β-THDOC, CDCA and LCA, which inhibit both 11β-OHSD and 5β-R activity, and one of which (CDCA) can confer mineralocorticoid actions upon the glucocorticoid, corticosterone.

Equivalents

Those skilled in the art will recognize, or be able to ascertain using no more than routine experimentation, numerous equivalents to the specific procedures described herein. Such equivalents are considered to be within the scope of this invention and are covered by the following claims.

What is claimed is:

1. An antibody specific for a human glycyrrhetinic-acid-like factor wherein said factor is not glycyrrhetinic-acid or a metabolite thereof, and wherein said factor has the following characteristics:

a) is isolatable from human urine;

b) is water-soluble;

c) is not extractable from aqueous solution into ethyl acetate;

d) is resistant to trypsin treatment;
e) inhibits hepatic and renal 11β-hydroxy steroid dehydrogenase (11β-OHSD);
f) inhibits 5β-steroid reductase; and
g) elutes from a reverse phase high performance liquid chromatograph as two major fractions of 11β-OHSD and 5β steroid reductase inhibitory activity under the following conditions: a non-linear methanol water gradient commencing with 30% methanol which is increased linearly to 40% methanol at 400 secs.; 60% methanol at 1900 secs.; and 100% methanol at 2000 secs., wherein the first fraction elutes at 34–38% methanol and the second fraction elutes at 46–47% methanol.

* * * * *